United States Patent
Scripca et al.

[19]

[11] Patent Number: 6,096,560
[45] Date of Patent: Aug. 1, 2000

[54] METHOD AND APPARATUS FOR DETERMINING THE CONCENTRATION OF A TARGET GAS USING AN OPTICAL GAS SENSOR SYSTEM

[75] Inventors: Lucian E. Scripca, San Diego; Mark K. Goldstein, Del Mar, both of Calif.

[73] Assignee: Quantum Group, Inc., San Diego, Calif.

[21] Appl. No.: 09/198,765

[22] Filed: Nov. 24, 1998

[51] Int. Cl.$^7$ .................................................. G01N 21/59
[52] U.S. Cl. ........................ 436/164; 436/167; 436/134; 422/91; 422/119; 356/437
[58] Field of Search .................. 422/86, 91, 93, 422/119; 436/50, 55, 134, 164, 167; 356/433, 434, 435, 437

[56] References Cited

U.S. PATENT DOCUMENTS

| | | | |
|---|---|---|---|
| 3,860,818 | 1/1975 | Stalder et al. | 250/343 |
| 4,464,653 | 8/1984 | Winner | 340/501 |
| 4,617,277 | 10/1986 | Bohl | 436/34 |
| 4,818,705 | 4/1989 | Schneider et al. | 436/164 |
| 5,567,622 | 10/1996 | Jaduszliwer et al. | 436/106 |
| 5,573,953 | 11/1996 | Marnie et al. | 436/164 |
| 5,597,534 | 1/1997 | Kaiser | 422/82.02 |
| 5,747,348 | 5/1998 | Jaduszliwer et al. | 436/106 |

*Primary Examiner*—Jeffrey Snay
*Attorney, Agent, or Firm*—Christie Parker & Hale, LLP

[57] ABSTRACT

The concentration of a target gas is determined in an optical gas sensor system having an array of optical gas sensors wherein each sensor has a different sensitivity range for a target gas. An active sensor is selected from the array of optical gas sensors by determining which sensor has an optical transmittance value between 0% and 100%. Optical transmittance values of the active sensor are differentiated with respect to time. Concentration of the target gas is calculated as a function of both the rate of change of optical transmittance and the value of the optical transmittance at the beginning of the period over which the transmittance is differentiated. When a hazardous gas such as carbon monoxide is the target gas an alarm can be given when a threshold concentration is exceeded. Preferably, the transmittance values are converted to digital signals and processed in an eight-bit microprocessor to determine target gas concentration.

12 Claims, 5 Drawing Sheets

METHOD AND APPARATUS FOR DETERMINING THE CONCENTRATION OF A TARGET GAS USING AN OPTICAL GAS SENSOR SYSTEM

BACKGROUND

Over the past decade, public awareness of the harmful effects and dangers of hazardous gases in the air has increased, resulting in a growing demand for accurate, inexpensive, and compact devices that detect such gases.

Conventional battery operated, portable gas detection devices typically use electrochemical cells for sensing the presence of hazardous gases. Such units are expensive ($500 to $1000 per unit), require periodic calibration, and frequent sensor and battery replacement. Other portable gas detection devices use semiconductor based, metal oxide sensors which require large amounts of power to operate. Such units are not able to operate for reasonable periods of time (e.g. more than a few hours) on batteries. Thus, there remains an unmet need for a low cost, reliable, accurate, easy to use, low power, battery powered unit for detecting hazardous gases.

A variety of optical gas sensors for detecting the presence of hazardous gases, especially carbon monoxide ("CO"), are known. Exemplary optical gas sensors are described in U.S. Pat. Nos. 5,063,164; 5,302,350; 5,346,671; and, 5,405,583 the contents of which are hereby incorporated by reference. An improved optical gas sensor system has been made by optically combining gas sensors having a response over a wide range of humidity and temperature conditions as disclosed in U.S. Pat. No. 5,618,493, the contents of which are also hereby incorporated by reference.

Generally, optical gas sensors include a self-regenerating, chemical sensor reagent impregnated into or coated onto a semi-transparent substrate. The substrate is typically a porous monolithic material, such as silicon dioxide, aluminum oxide, aluminosilicates, etc. Upon exposure to a predetermined target gas, the optical characteristics of the sensor change, either darkening or lightening depending on the chemistry of the sensor.

Battery powered, target gas detection devices utilizing optical gas sensors are commercially available and have met with great market success. Such devices include at least one sensor placed in a light path between a light emitting means and a light detecting means. The light detecting means monitors the optical characteristics of the sensor by measuring the level of light transmitted through the sensor. Electronic components of the device are devised so that when the detected level of transmitted light falls below a predetermined fixed level, an alarm or other warning means is activated.

Beyond the activation of a warning or alarm when hazardous conditions exist, users of such hazardous gas detection devices often have a need or desire to know other relevant information such as concentration, time weighted average (TWA), total dose received in a given time period, and rate of change of the concentration of the target gas.

BRIEF SUMMARY OF THE INVENTION

Concentration of a target gas is digitally determined using an optical gas sensor system having an array of optical gas sensors. Each of the sensors has a different concentration sensitivity range for the target gas. The sensors in the array are exposed to an environment which may contain the target gas and an active sensor is selected from the array such that the active sensor sensitivity range corresponds to the target gas concentration. A plurality of optical density values of the active sensor are determined and differentiated with respect to time between a first time and a earlier second time to determine the rate of change of the optical density between the two times. The concentration of the target gas is calculated using the value of the rate of change and the value of the optical transmittance at the first time. If desired, a tangible output event can be provided when the concentration of the target gas exceeds a threshold representative of a hazardous condition.

DETAILED DESCRIPTION

Figure 1:
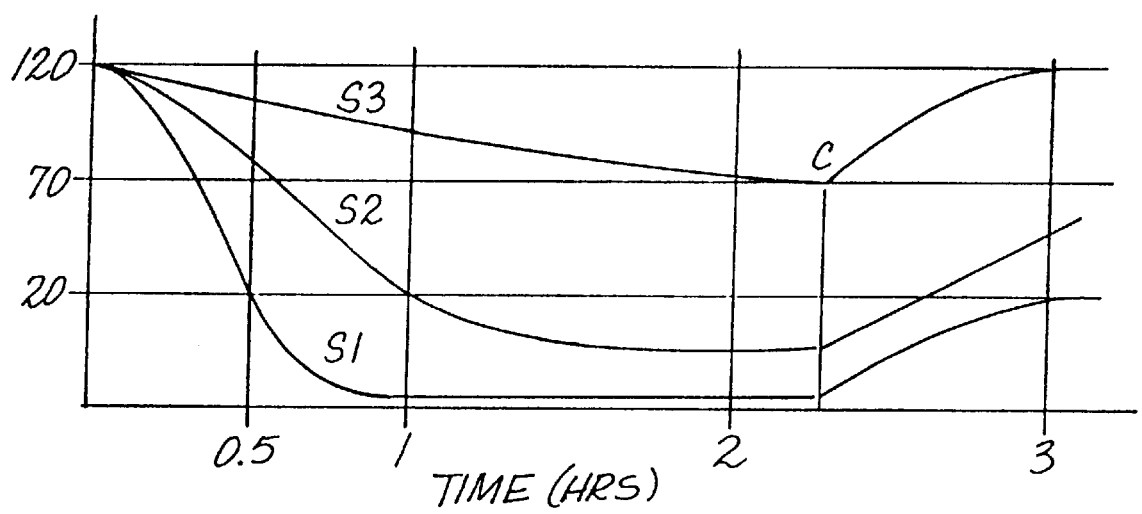
FIG. 1 graphically illustrates the optical response of a three different optical gas sensors upon exposure to a target gas.

The present invention is drawn to a method and apparatus for digitally determining the concentration of a target gas using an optical gas sensor system. Accurate measurements made over a broad range of target gas concentrations are achieved by measuring the optical characteristics of a plurality of optical gas sensors contained within an optical gas sensor assembly.

Optical gas sensors, such as those noted in the above referenced documents, can be made to detect a wide variety of hazardous gases. For the purposes of the present disclosure, carbon monoxide (CO) is used as an exemplary target gas to illustrate the principles of the present invention. It will, hazardous gases, such as ethylene oxide, mercury vapor, hydrogen sulfide, among others, may be substituted for or used in addition to the carbon monoxide sensor. Thus, such variations and alternate embodiments are considered to be within the scope of the present invention.

The response of an optical gas sensor to hazardous gas is determined by the formulation of the impregnating chemical sensing reagent and the characteristics of the substrate. For any given sensor formulation, the amount of the light transmitted by the sensor, which in the present case is a carbon monoxide (CO) sensor, has been found to have a linear static component and an exponential dynamic component.

The static component is expressed by the equation:

$$\{k_1[I_0 - I(t_n)] + k_2\}$$

wherein $k_1$ is a constant value dependent upon the sensor formulation; $k_2$ is a constant value corresponding to the predetermined threshold of the sensor; $I_0$ is the optical transmittance in the absence of CO; and $I(t_n)$ is the optical transmittance at time $t_n$.

In sensors exposed to fixed concentrations of CO for long periods of time (more than a few hours), the optical transmittance of the sensor becomes a constant value described by the above equation. This equation reflects the establishment of an equilibrium between the chemical sensor reagent of the sensor and the CO present in the surrounding air. Thus, when the sensor is at equilibrium with the surrounding environment, the concentration of CO can be readily determined given a value of $I(t_n)$ and knowledge of $k_1$, $I_0$ and $k_2$ for that particular sensor formulation.

The second component is an exponential, dynamic component expressed by the equation:

$$\exp\{k_3[I(t_n)-I(t_{n-1})]/[t_n-t_{n-1}]\}=\exp\{k_3[dI(t)/dt]\}$$

wherein: $k_3$ is a constant dependent upon the formulation of the chemical sensor reagent; $I(t_n)$ is the optical transmittance at time $t_n$; $I(t_{n-1})$ is the optical transmittance at time $t_{n-1}$ previous to $t_n$; and $[dI(t)/dt]$ is the first derivative of the optical transmittance over the time period t.

Upon exposure of the sensor to a different concentration of CO, be it higher or lower, the previously established equilibrium is upset. This causes a change in the optical transmittance of the sensor that is described by the dynamic component equation given above.

Given the above equations, one is able to calculate the concentration of the target gas, in this case CO, at any particular time. This is achieved by the combination of the static and dynamic equations given above, thus giving:

$$[CO]=\{k_1[I_0-I(t_n)]+k_2\}\exp\{k_3[dI(t)/dt]\}$$

wherein: [CO] is the concentration of CO; $k_1$ is a constant value dependent upon the sensor formulation; $k_2$ is a constant value corresponding to the predetermined threshold of the CO sensor; $I_0$ is the optical transmittance in the absence of CO; $I(t_n)$ is the optical transmittance at time $t_n$; $k_3$ is a constant dependent upon the formulation of the chemical sensor reagent; and, $[dI(t)/dt]$ is the first derivative of the optical transmittance over the time period t, also known as the rate of change in the optical transmittance.

The exponential term of the above equation can be approximated, using the first two or three terms of the Taylor series, thus giving the equation:

$$[CO]=\{k_1[I_0-I(t_n)]+k_2\}\{1+k_3[dI(t)/dt]\}$$

With this equation, the calculation of the concentration of CO at any time (t) can be accomplished quickly and easily. Further, one is able to determine concentration derived values, such as time weighted average (TWA), theoretical dose, total exposure over a predetermined time period, etc. Other expansions for solving exponential equations may be used, but the Taylor series appears to be most efficient in terms of the computational power required for precision results. The Taylor series converges rapidly and by solving for just the first three terms of the Taylor series, a precision of about 3 ppm can be obtained for gas concentration.

Given the above, one is able to detect a broad range (e.g. 10 ppm to 1000 ppm CO) of gas concentrations using a properly formulated sensor. It has been found, however, that a plurality of optical gas sensors, each sensor having a specific predetermined optimum concentration range and arranged to form a sensor array, is more accurate and more economical to implement. The principles of such a multi-sensor system are described below.

Carbon monoxide sensitive sensors are made by a process previously described, that is by the impregnation of a porous, semi-transparent monolithic substrate with a CO sensitive chemical reagent. A suitable impregnating chemical reagent is a mixture of chemical compounds containing at least one compound from each of the following groups: Group 1 comprising palladium compounds and their hydrates; Group 2 comprising molybdenum compounds and their hydrates; Group 3 comprising copper compounds and their hydrates; Group 4 comprising cyclodextrin molecular encapsulants; Group 5 comprising soluble chloride and bromide salts and their hydrates; Group 6 comprising halogenated acetic acid, and alkali metal and alkaline-earth metal salts of halogenated acetic acids; Group 7 comprising a soluble metal trifluoroacetylacetonate; and Group 8 comprising heteropolymetallic acids, their salts and hydrates.

Preferred Group 1 materials include those selected from the group consisting of palladium sulfate; palladium sulfite; palladium pyrosulfite; palladium chloride; palladium bromide; calcium, sodium and potassium salts of the tetrachloropallidate, bromotrichloropallidate, dibromodichloropallidate, tribromochloropallidate and tetrabromopallidate ions; and mixtures thereof.

Preferred Group 2 materials include those selected from the group consisting of silicomolybdic acid; salts of silicomolybdic acid; molybdenum trioxide; ammonium molybdate; alkali or alkaline earth salts of molybdate anion; and mixtures thereof.

Preferred Group 3 materials include those selected from the group consisting of copper sulfate; copper bromide; copper chloride; copper fluoride; copper iodide; copper trifluoroacetate; copper perchlorate; and mixtures thereof.

Preferred Group 4 materials include those selected from the group consisting of α-cyclodextrin; β-cyclodextrin; modified β-cyclodextrin; γ-cyclodextrin; cyclodextrins having an internal cavity of at least 5 Å ($5\times10^{-10}$ m); and mixtures thereof.

Preferred Group 5 materials include those selected from the group consisting of sodium, lithium, platinum, magnesium, calcium, strontium, beryllium, barium, zinc and mixtures thereof.

Preferred Group 6 materials include those selected from the group consisting of trichloroacetic acid; tribromoacetic acid; the sodium, potassium, calcium salts of trichloroacetate; the sodium, potassium, calcium salts of tribromoacetate; and mixtures thereof.

Preferred Group 7 materials include those selected from the group consisting of copper, calcium, magnesium, sodium, potassium, lithium and mixtures thereof.

Preferred Group 8 materials include those selected from the group consisting of compounds having the formula $H_4SiMo_{12-x}E_xO_{40}$, where E is selected from the group consisting: chromium, vanadium, cobalt, manganese, iron, niobium, tantalum and tungsten, and x has value between 2 and 6; silicotungstic acid; and mixtures thereof.

By replacing or partially replacing the silicomolybdate anion by other heteropolymolybdate anions in the chemical reagent used to make the sensors, the response threshold of a CO sensor can be controlled. Especially useful are heteropoly acids, their salts and hydrates selected from compounds having the general formula $H_4SiMo_{12-x}E_xO_{40}$, where E is selected from the group consisting: chromium, vanadium, cobalt, manganese, iron, niobium, tantalum and tungsten and x has value between 2 and 6; silicomolybdic acid; silicotungstic acid; and mixtures thereof.

It is believe that the introduction of other metals into the structure of the silicomolybdic acid retards the reduction of the molybdenum containing species by the palladium catalyst. By making this change, the sensor does not darken as readily upon exposure to low level concentrations of CO. Therefore by carefully adjusting the amount and the redox properties of the molybdenum containing compounds, the response threshold of the sensors can be controlled.

These sensors can be formulated so as to respond (i.e. darken) upon exposure to CO at or above a predetermined response threshold. Using these principles, one skilled in the art can make sensors having a controlled response threshold in excess of 500 ppm CO.

It has been found that sensors having low response thresholds (below 35 ppm) rapidly darken and become saturated when exposed to very high concentrations of CO (e.g. 100 ppm or greater). Further, sensors having a very high response threshold are only affected by high concentrations of CO. This principle is generally illustrated in FIG. 1 which shows the typical response of three different sensors to 200 ppm CO over several hours. Sensor 1 (designated S1) having a low response threshold (e.g. 10 ppm) crosses the alarm point ($I_{rel}$<20) after about 30 minutes and becomes saturated ($I_{rel}$<1) within one hour. Sensor 2 (designated S2) having a moderate response threshold (e.g. 60 ppm) darkens enough to fall below the alarm point ($I_{rel}$=20) after about one hour. Sensor 3 (S3), having a high response threshold (e.g. 150 ppm) darkens slightly over the course of two or more hours but not sufficiently to trigger an alarm response.

Upon reduction of the CO level to about 15 ppm at about 2¼ hours, all of the sensors begin to regenerate and recover (i.e. lighten) at their own rate. Sensor 3 recovers rapidly and is completely regenerated ($I_{rel}$=100) within one hour. Sensor 2 recovers at a more moderate rate and Sensor 1 only partially recovers. Upon exposure to clean air all of the sensors regenerate and recover their original color ($I_{rel}$=100).

Given the above, one skilled in the art will appreciate and be able to determine empirically the values of $k_1$, $k_2$ and $k_3$ used in the above equations for any given sensor formulation and thereby be able to calculate the concentration of target gas as previously disclosed. Such a person would also know that the values of $k_1$, $k_2$ and $k_3$ used to calculate target gas concentration upon darkening of the sensor may be different from the value of $k_1$, $k_2$ and $k_3$ used to calculate target gas concentration upon lightening of the sensor. The present invention is directed to a method and apparatus in which an array of optical gas sensors are used to accurately determine the concentrations of target gas in the surrounding environment.

Figure 2:
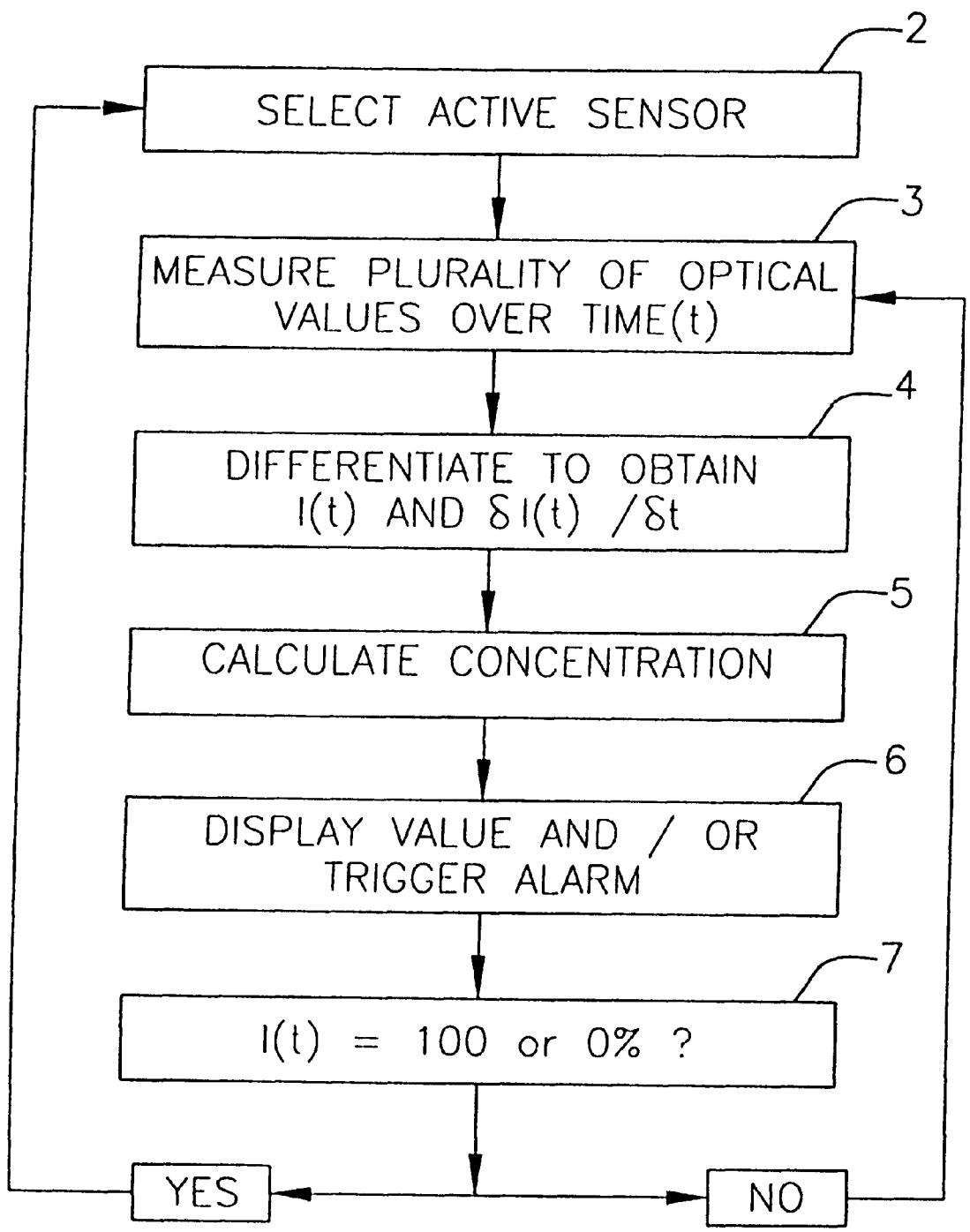
FIG. 2 schematically shows the preferred method of the present invention.

As schematically shown in FIG. 2, the method of the present invention includes selecting the active sensor from the optical gas sensor array, measuring a plurality of optical transmittance values of the active sensor, differentiating the plurality of measurements over time to calculate the rate of change in the optical transmittance of the active sensor between a first time and an earlier second time (i.e. dI/dt) and the value of optical transmittance of the active sensor at the first time (i.e. I(t)), and calculating the concentration of target gas at time $t_n$ as a function of both I(t) and dI/dt. The target gas concentration information is used to determine if a hazardous condition exists in the surrounding environment, thus triggering an alarm. The calculated concentration value may also be displayed for the user or used to calculate derived values such as time weighted average (TWA), theoretical dose, exposure over a given time period, etc.

U.S. Pat. No. 5,573,953 discloses a method for determining carbon monoxide concentration in a self regenerating optical sensor by determining the rate of change of light transmission through the sensor. Transmitted light falls on a photodetector and the photodetector current charges a capacitor. The capacitor charge is sampled as a digital reading to determine the darkening of the sensor. Successive readings, in essence, differentiate over time to determine the rate of change of optical transmission of the sensor. The rate of change information is used to determine the concentration of carbon monoxide and whether an alarm should be sounded. This approach is employed to avoid measuring the absolute value of optical transmission of the sensor which may be influenced by variables in addition to carbon monoxide concentration.

In the technique employed in practice of this invention the value of optical transmission and the rate of change of optical transmission are both employed for calculating carbon monoxide concentration. Since a number of sensors with different sensitivity ranges are employed in a preferred practice of this invention, it is preferred to sample optical properties and calculate rate of change digitally. It will be apparent that rate of change could be determined as in U.S. Pat. No. 5,573,953 and converted to a digital signal somewhat later for determination of carbon monoxide concentration.

An additional feature of the present method is the automatic selection of the active sensor from the optical gas sensor array. During this selection process, the optical transmittance is determined for each sensor. If the optical transmittance of the first sensor reflects 0% or 100% optical transmittance, that sensor is excluded and another reading is made on the next sensor in the array. If the first sensor has an optical transmittance between, but not equal to 0% or 100%, the first sensor is selected as the active sensor and a second measurement of optical transmittance $I(t_n)$ is made after a predetermined time. The optical transmittance values of the active sensor are differentiated over time and the rate of change in optical transmittance is calculated. If at any time the optical transmittance of the active sensor becomes 0% or 100%, the search for an active sensor is initiated. If all sensors in the array have an optical transmittance of 0%, an immediate danger to life exists and an alarm will sound with the display flashing a warning signal, such as 911.

It will be recognized in this description that 100% optical transmittance does not represent absolute transparency. It refers to the amount of transmittance of light through the sensor in the absence of any reaction to the target gas. Likewise, 0% transmittance may refer to a substantially opaque sensor or be a somewhat arbitrary end point below which the photodetectors may yield an unreliable result.

Development of the software code needed to carry out the above method is straightforward and clearly within the skill of a typical programmer. Exemplary software code for use with two 8 bit microprocessors is given in Appendix A, to U.S. Provisional Patent Application No. 60/026,534, the contents of which are hereby incorporated by reference.

The above description uses an array of optical CO sensors (e.g., CO being the target gas) to illustrate the method of the present invention. It will readily be appreciated that this novel method of accurately obtaining target gas concentration information can be used with any set of optical responding sensing material.

Figure 3:
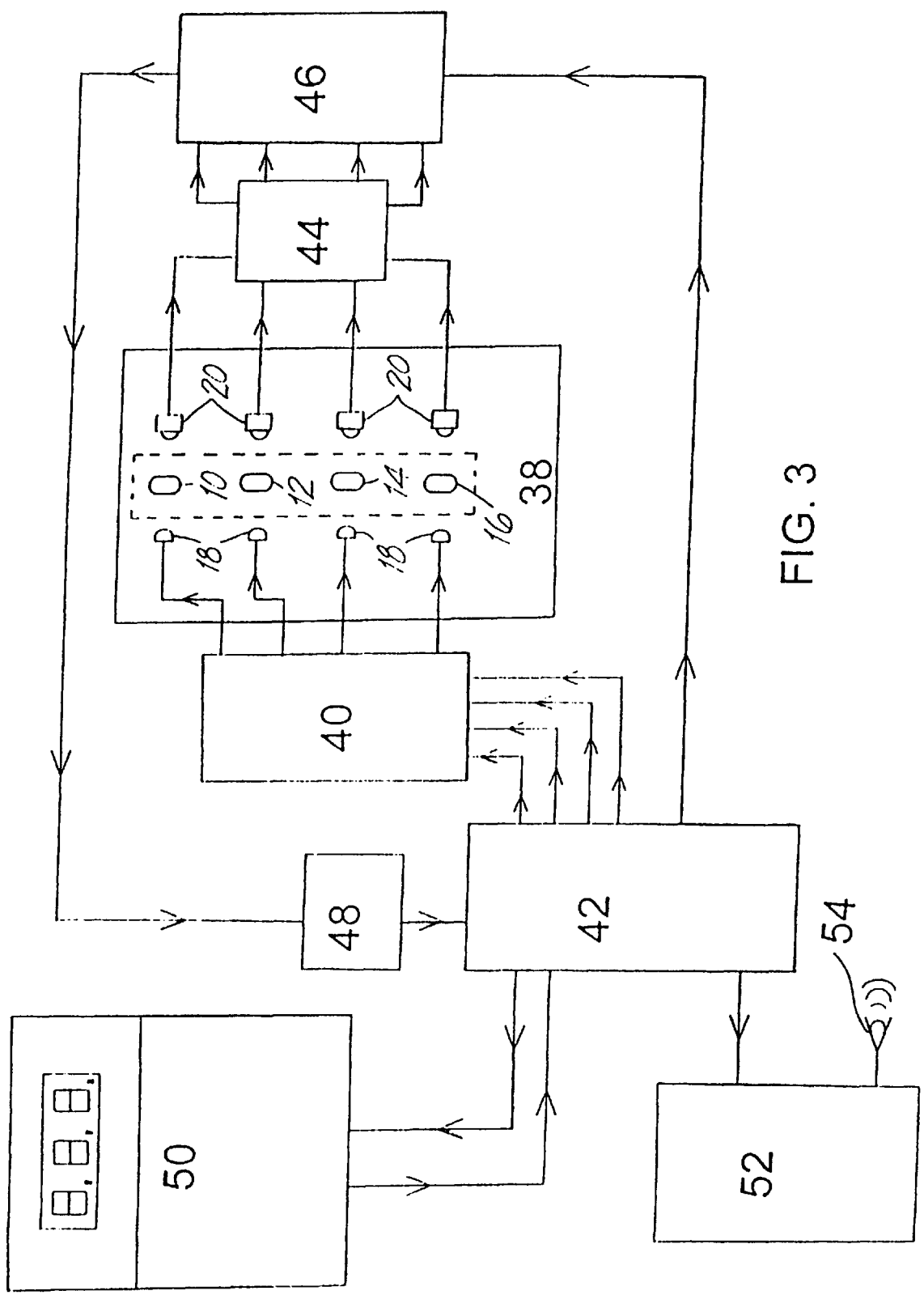
FIG. 3 is a block diagram of the basic components within an embodiment of a digital gas detection device utilizing the method of the present invention.

An exemplary apparatus useful in the implementation of the earlier disclosed principles and the above method is schematically illustrated in FIG. 3. As shown, the apparatus comprises several functional "blocks", each block carrying out one or more tasks as generally described below.

The target gas sensing block 38 comprises a plurality of optical gas sensors 10, 12, 14 and 16 having different response thresholds which are optically aligned between a plurality of light emitting means 18, such as an array of infrared light emitting diodes (IR-LEDs), and a plurality of corresponding light detecting means 20, such as an array of photodiodes. Each target gas sensor is located so that the light generated by the matching IR-LED passes through the sensor. The attenuated light transmitted by the sensor is measured by a corresponding photodiode. As shown, the sensors are aligned so that the light passes axially through the sensor. Clearly, other orientations of the sensors relative to the LEDs and photodiodes and the optical path are suitable and will substantially achieve the same result and thus are considered within the scope of the present invention. Each IR-LED-Sensor-Photodiode triad is assigned to a different measurement range. In an example, the first set measures 30–100 ppm; the second set measures 100–200 ppm; the third set measures 200–400 ppm; and, the fourth set measures 400–1000 ppm. If desired the sensitivity ranges may overlap at the ends.

Figure 4:
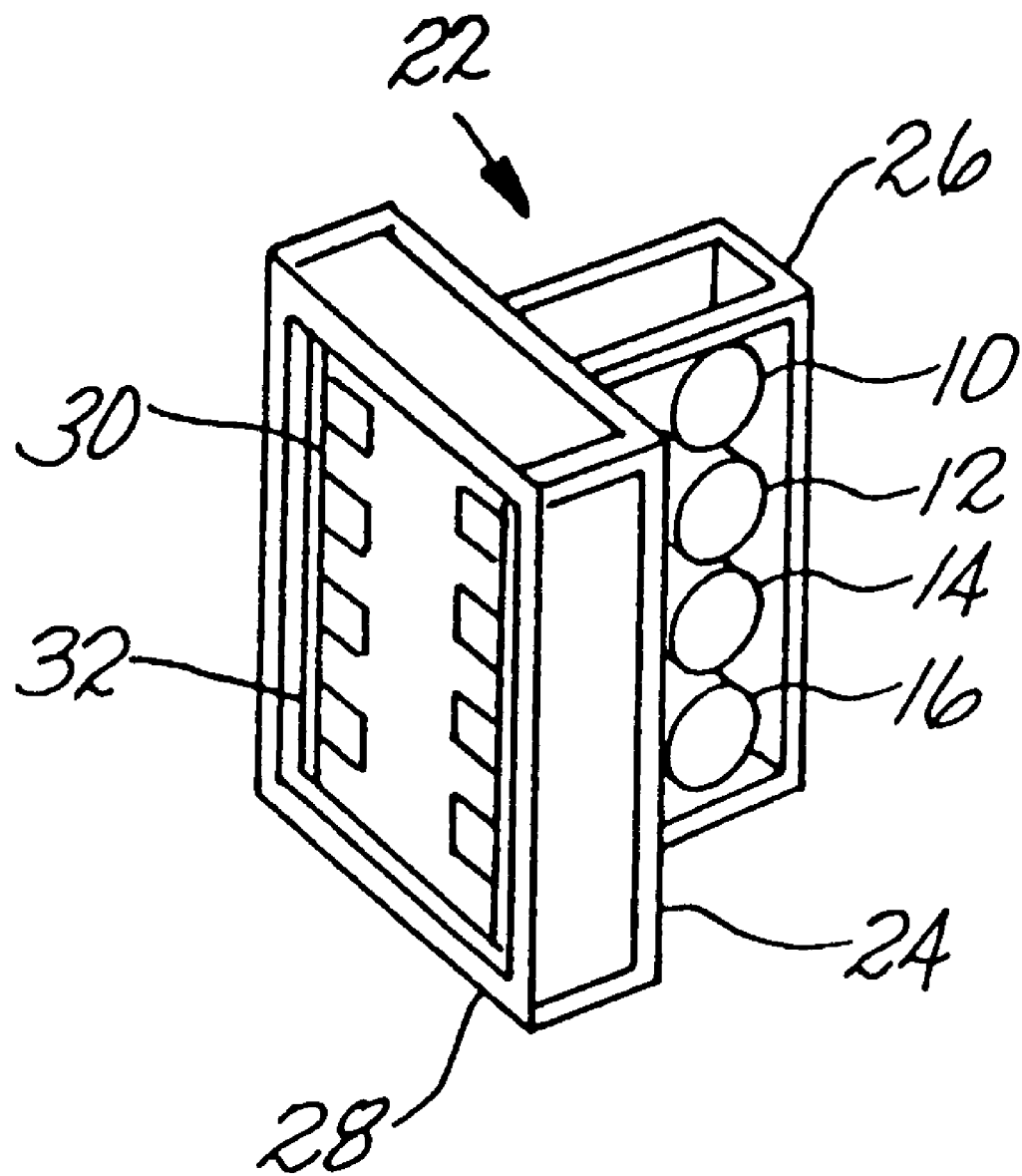
FIG. 4 is a elevational view of an optical gas sensor assembly used in an embodiment of the present invention.

The optical gas sensors 10, 12, 14, and 16 are part of an optical gas sensor assembly illustrated in FIG. 4, and generally designated by arrow 22. The optical gas sensor assembly 22 includes a housing 24 having a lower end 26 that holds the sensors in alignment between the LED and the photodiode arrays. The housing 24 has an upper end 28, which is in fluid communication with the lower end, and may contain filtering or gettering materials (not shown). Such filtering or gettering materials prevent dust, excess moisture, and other harmful agents from reaching the optical gas sensor 10, 12, 14, and 16. The gettering materials and sensors are held in place by a perforated cap 30 which is secured by way of a retaining ring 32.

Power is delivered to each infrared light emitting diode by a standard LED power circuit collectively designated as the LED power block 40.

A central microprocessor 42 controls and provides the necessary signals to the LED power block so that only the LED for the active sensor is powered. During the active sensor search mode, the central microprocessor ensures that at only one IR-LED has power at any particular moment.

After the light from the IR-LED has been attenuated by the sensor it is detected by a corresponding photodiode 20. The signal from the photodiode of the active sensor is amplified by an operational amplifier 44 and the amplified signal sent to an analog demultiplexer 46. The central microprocessor sends a two bit binary address to the demultiplexer selecting the output signal for the active sensor.

The analog signal from the demultiplexer is converted to a digital signal by an analog to digital converter 48. The central microprocessor also controls and provides the necessary signals to the analog to digital converter, such as enable and clock, and collects the eight bit word in a serial mode. The eight bit byte is fed to the central microprocessor which adds a start bit and a stop bit to the eight bits received from the analog to digital conversion block and sends it to the math-processor and display block 50.

Upon receipt of the input signal from the central microprocessor, the math-processor and display block 50 calculates a concentration value of CO using the equation previously discussed. The concentration value may be displayed on a digital display or used internally to calculate concentration derived values such as TWA, dose, etc. If the central microprocessor and the microprocessor in the math-processor and display block run independently, they communicate using a synchronization protocol. In this case, the math-processor and display block, spends most of the time driving the digital display, or processing the data into the equation. At the end of a cycle, a signal is sent by the math-processor and display block to the central microprocessor indicating that an information byte is to be sent and the central processor must start a data conversion cycle. When the conversion cycle is finished, the central microprocessor sends a message back to the math-processor and display block, signalling that it is ready to transmit the data. The data is transmitted and the math-processor and display block starts another mathematical processing cycle and display cycle. The display cycles are interrupted, from time to time, for receiving another byte of information, however, the interruption is too short for a user to notice.

The calculated value is used to determine if a hazardous condition exists and if an alarm should be triggered. Should an alarm condition exist, the math-processor and display block sends an alarm signal to the central microprocessor. Upon receipt of an alarm signal, the central microprocessor activates the hex logic inverter in a oscillator configuration used in the enunciator block 52 to drive a piezo-electric speaker 54.

Figure 5:
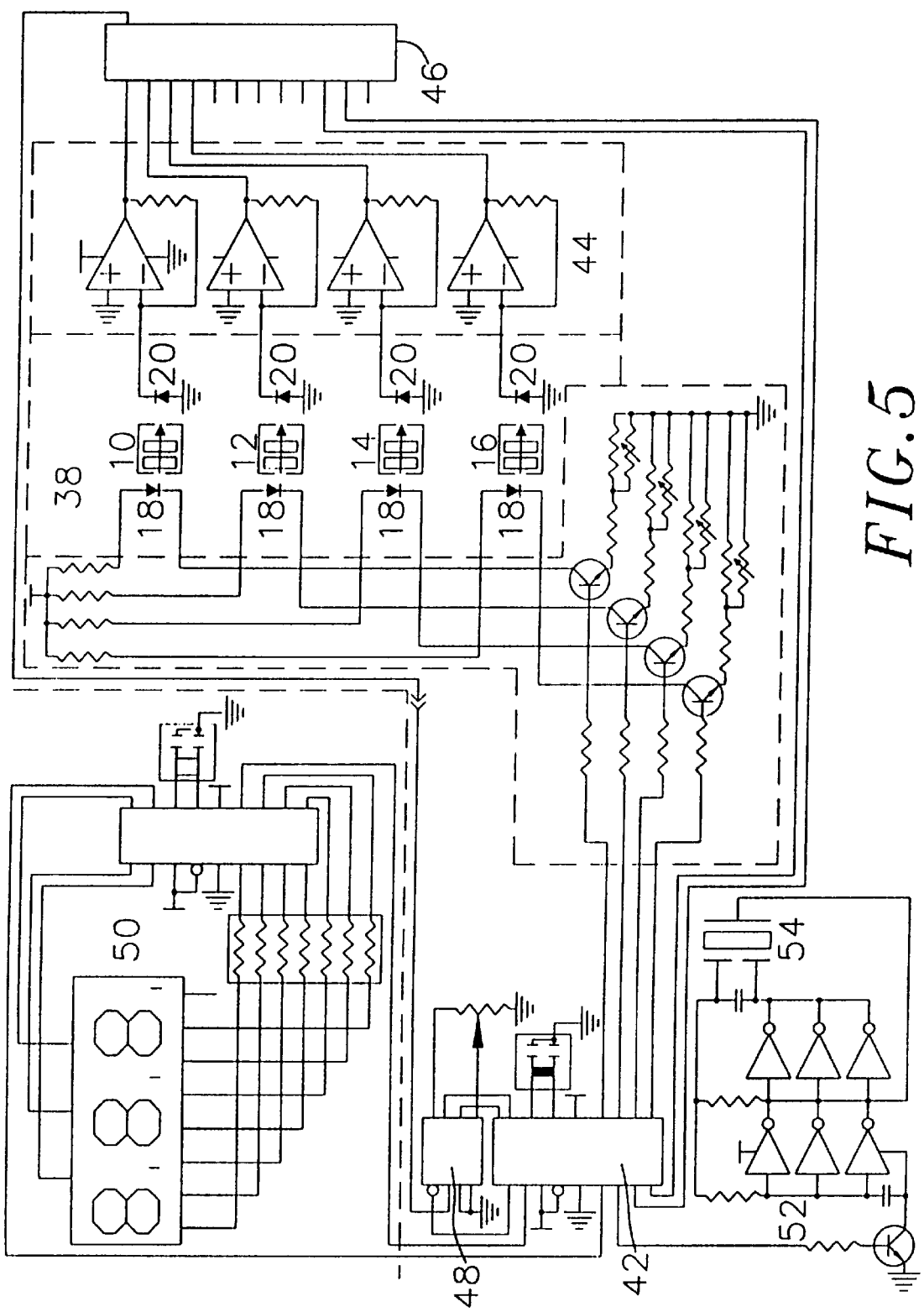
FIG. 5 is a detailed circuit diagram of an embodiment of the present invention.

A specific example of the above described digital gas alarm is shown in FIG. 5 using two eight bit microprocessors and an analog to digital converter to detect CO. The target gas sensor block contains a set of four CO sensors designed to cover a range of 0 to 1000 ppm CO concentration. The measurement range is divided into four ranges to improve accuracy of the calculated CO concentration while utilizing an inexpensive eight bit A/D conversion microprocessor. An alternative is to use a 16 bit A/D converter and a sixteen bit central microprocessor. However, the price of these devices are about 20 times higher than the eight bit version, therefore it is easier and more economical to divide the measuring range into four sub-ranges, e.g., 0 to 100 ppm, 100 to 200 ppm, 200 to 400 ppm and 400 to 1000 ppm.

One of the problems encountered in the implementation of the equation is that posed by the use of eight bit binary numbers. If single precision arithmetic is employed, all terms of the operations and all the results must be numbers between 0 and 255. Because there are operations where the first, second and sometimes the third decimal must be considered, the use of single precision eight bit arithmetic is not possible. Double precision arithmetic can be used to avoid this, but the size of the final program exceeds by far the memory of the chosen microprocessor. Due to the nature of the final display, it is easier to use the decimal arithmetic, since the displayed result is a base 10 number.

When the information byte is received by the microprocessor in the math-processor and display block, it is first converted into a decimal number, loading the number into three different registers. For example, loading the number 123 so that the number 1 is in a register for hundreds, the number 2 is in a register for tens and the number 3 is in a register for units.

Eight registers are employed, four for the first operand and four for the second operand. Another four registers are used as a big work register. Since operations are much easier to implement into the program, the operands and the work register are set to have four registers: thousands, hundreds, tens and units in order to easily process large numbers.

One critical operation is multiplying by parameter $k_3$ because it is a number between 0 and 1 and most important are the second and third decimal places. In order to use this number, e.g., when multiplying 123 by $k_3$, when $k_3$=0.045, the number 123 is loaded as previously noted and then the number 45 is loaded in the second operand. Multiplication is performed and the result, the number 5535, is loaded in the work register. The number 5535 must then be divided by 1000. This is easily done by shifting the work register three times to the right. The end result will be 0005, meaning a value of 5 will be found in the units register. In a similar way, the remaining calculations are made and the final result is moved to a set of display registers.

Clearly, a variety of microprocessors, components and other circuit elements can be used to implement the present invention, including those with built-in analog to digital converters, built-in liquid crystal display drivers and so on. Further, although transmittance of light is used herein to illustrate the present invention, one skilled in the art would realize that other means of determining the optical characteristic of the sensor, such as absorption, reflection, refraction, etc. could be used. Therefore, such embodiments are considered to be within the scope of the present invention.

The application of the present invention to a wide variety of products is not intended to be limited to residential CO detectors. Other application are possible including, but not limited to: residential detectors, personnel monitors, medical gas monitoring units, breath diagnostic units, industrial HVAC control units, and combustion exhaust sensing devices.

The present invention has been described in relation to limited examples and embodiments which are for illustrative purposes and are not intended to limit the scope of the invention. Although a number of specific embodiments, methods, and compositions have been described and illustrated herein, it will be apparent to one skilled in the art that further variations are possible. Thus, the present invention may be embodied and practiced otherwise than specifically described herein, and therefore the scope of the invention is defined by the following claims.

What is claimed is:

1. A method of digitally determining presence or absence of a hazardous condition due to the concentration of a target gas using an optical gas sensor system, comprising the steps of:

selecting an active sensor from an array of optical gas sensors;

measuring a plurality of optical transmittance values of the active sensor upon exposure to a predetermined target gas;

differentiating the plurality of optical transmittance values with respect to time between a first time and a earlier second time to determine the value of the rate of change of the optical density between the two times;

calculating a concentration value of the target gas using the value of the rate of change and the value of the optical transmittance at the first time; and providing a tangible output event when the concentration value exceeds a threshold representative of a hazardous condition.

2. A method as recited in claim 1, further comprising comparing the calculated concentration value of the target gas with a predetermined alarm value and triggering an alarm if a hazardous condition exists.

3. A method as recited in claim 1, wherein selecting an active sensor from an array of optical gas sensors comprises measuring the optical transmittance of each optical sensor in the array; and selecting the active sensor by determining which sensor has an optical transmittance value between 0% and 100%.

4. A method as recited in claim 1 wherein the concentration of gas is calculated employing a Taylor series expansion.

5. A method for providing an alarm in the event of a hazardous concentration of a target gas comprising the steps of:

selecting an active sensor from an array of optical gas sensors, each of the sensors having a sensitivity range different from the other sensors in the array;

measuring a plurality of optical transmittance values of the active sensor;

differentiating the plurality of measurements over time to calculate the rate of change in the optical transmittance of the active sensor between a first time and an earlier second time and the value of optical transmittance of the active sensor at the first time;

calculating the concentration of target gas at the first time as a function of both the rate of change of optical transmittance and the value of the optical transmittance of the active sensor at the first time for determining if a hazardous condition exists in the surrounding environment; and triggering an alarm in the event a hazardous condition exists.

6. A method of digitally determining presence or absence of a hazardous condition due to the concentration of a target gas using an optical gas sensor system, comprising the steps of:

exposing a plurality of optical gas sensors to an environment being monitored for gas concentration, each of the sensors being sensitive to a different gas concentration range from others of the gas sensors;

determining an optical property of each of the sensors which is a function of gas concentration;

selecting as an active sensor, one of the sensors which senses a gas concentration within its sensitivity range; and determining the gas concentration of the environment by calculations based on the optical property and rate of change of the optical property by the active sensor.

7. A method as recited in claim 6 wherein selecting an active sensor from the plurality of optical gas sensors comprises:

measuring the optical transmittance of each optical sensor; and selecting the active sensor by determining which sensor has an optical transmittance value between 0% and 100%.

8. Apparatus for digitally determining the concentration of a target gas using an optical gas sensor comprising:

a plurality of optical gas sensors in fluid communication with a surrounding environment;

means for selecting an active sensor from the plurality of optical gas sensors;

means for measuring a plurality of optical transmittance values of the active sensor upon exposure to a predetermined target gas;

a microprocessor programmed for differentiating the plurality of optical transmittance values with respect to time between a first time and a earlier second time to determine the value of the rate of change of the optical density between the two times; and means for calculating a concentration value of the target gas using the value of the rate of change and the value of the optical transmittance at the first time.

9. Apparatus according to claim 8 further comprising means for determining whether the concentration value of the target gas exceeds a threshold of a hazardous condition and means for providing a tangible output in the event the concentration value exceeds the threshold.

10. Apparatus according to claim 8 wherein the means for selecting an active sensor comprises means for determining whether a sensor has an optical transmittance between, but not equal to 0% or 100%.

11. Apparatus according to claim 8 wherein the gas sensors comprise:

a first sensor having a sensitivity to a target gas concentration in the range of from (a) to (b);

a second sensor having a sensitivity to a target gas concentration in the range of from (b) to (c); and a third sensor having a sensitivity to a target gas concentration in the range of from (c) to (d), where (a)<(b)<(c)<(d).

12. Apparatus for digitally determining the concentration of a target gas using an optical gas sensor comprising:

a plurality of optical gas sensors in fluid communication with a surrounding environment, each of the sensors being sensitive to a different target gas concentration range from others of the gas sensors;

a light source and a photodetector for determining a level of optical transparency of each of the sensors which is a function of target gas concentration;

means for selecting one of the sensors which senses a target gas concentration within its sensitivity range as an active sensor; and a microprocessor for calculating target gas concentration as a function of both the optical transparency of the active sensor and rate of change of the optical transparency of the active sensor.

* * * * *